United States Patent
Boll et al.

(10) Patent No.: US 7,066,930 B2
(45) Date of Patent: Jun. 27, 2006

(54) ARRANGEMENT FOR THE TREATMENT OF BARRETT'S ESOPHAGUS

(75) Inventors: James H. Boll, Jamaica Plain, MA (US); George Cho, Hopkinton, MA (US)

(73) Assignee: Cynosure, Inc., Westford, MA (US)

( * ) Notice: Subject to any disclaimer, the term of this patent is extended or adjusted under 35 U.S.C. 154(b) by 369 days.

(21) Appl. No.: 10/118,283

(22) Filed: Apr. 8, 2002

(65) Prior Publication Data
US 2003/0191363 A1 Oct. 9, 2003

(51) Int. Cl.
*A61B 18/18* (2006.01)

(52) U.S. Cl. .............................. 606/15; 606/17; 607/88; 607/89; 600/101; 600/108; 600/160; 600/167; 604/20; 604/21; 128/898

(58) Field of Classification Search .............. 606/13–17; 602/88–90, 92; 600/101, 108, 114, 118, 160–163, 600/166, 167; 604/19–21, 27, 28, 48; 128/898
See application file for complete search history.

(56) References Cited

U.S. PATENT DOCUMENTS

| | | | | |
|---|---|---|---|---|
| 5,421,337 A | * | 6/1995 | Richards-Kortum et al. ..... | 128/665 |
| 6,086,558 A | * | 7/2000 | Bower et al. ............. | 604/96.01 |
| 6,394,949 B1 | * | 5/2002 | Crowley et al. ............. | 600/127 |
| 6,405,732 B1 | * | 6/2002 | Edwards et al. ............. | 128/898 |
| 6,409,723 B1 | * | 6/2002 | Edwards ...................... | 606/41 |
| 6,454,790 B1 | * | 9/2002 | Neuberger et al. ............ | 607/88 |
| 2003/0158550 A1 | * | 8/2003 | Ganz et al. ................. | 606/41 |

OTHER PUBLICATIONS

"Experimental PDT to Prevent Esophegus Cancer;" 1996. See http://www.bli.uci.edu/pubs/96fall.pdf.*
"Innovative Non–Surgical Treatment for Barrett's Esophagus ;" Jul., 1995. See http://www.pslgroup.com/dg950728.htm.*
Panjehpour M et al "Spectroscopic diagnosis of esophageal cancer: new classification model, improved measurement system." PubMed; Gastrointest Endosc. 1995 Jun.;41(6):577–81.*
Overholt BF et al. "Balloon photodynamic therapy of esophageal cancer: effect of increasing balloon size." PubMed; Lasers Surg Med. 1996;18(3):248–52.*
Ertan et al. "Esophageal Adenocarcinoma Associated with Barrett's Esophagus: Long–term Management with Laser Ablation," Am. J. Gastro. 90:2201–2203, 1995.*

* cited by examiner

*Primary Examiner*—A. Farah
(74) *Attorney, Agent, or Firm*—Hamilton, Brook, Smith & Reynolds, P.C.

(57) ABSTRACT

A method for the treatment of Barrett's Esophagus of a patient having endothelial esophageal complications. The treatment comprises connecting a wavelength specific light source to an elongated light guide having a distal end, the light guide arranged within a lumen of a steerable endoscope, guiding the endoscope into the esophagus of the patient, energyzing the light source, and manipulating the distal end of the light source onto a target on the endothelial complications inside of the patient's esophagus for the selective thermolysis of the target in the esophagus, thereby reverting the red secretory esophageal lining to a normal lining.

26 Claims, 8 Drawing Sheets

ARRANGEMENT FOR THE TREATMENT OF BARRETT'S ESOPHAGUS

BACKGROUND OF THE INVENTION

1. Field of the Invention

The present invention relates to the apparatus and the method of using that apparatus for the treatment of Barrett's Esophagus, and more particularly the utilization of a light apparatus to accomplish that treatment.

2. Prior Art

A condition known as Barrett's Esophagus, develops in some people who have chronic gastroesophageal reflux disease (GERD) or otherwise known as inflammation of the esophagus (esophagitis).

The esophagus is a muscular, membranous tube, about 25 cm long, through which food passes from the pharynx at the rear of the mouth, into the stomach.

The inner mucosa of the esophagus is lined with non-keratinized stratified squamous epithelium arranged in longitudinal folds. A number of mucous glands in the mucosa and submucosa provide a film of lubricating mucus to ease the passage of food to the stomach. The submucosa also contains blood vessels. The middle muscular's externa consists wholly of striated voluntary muscle in the upper third of the esophagus, a combination of smooth and striated muscle in the middle third, and wholly smooth muscle in the lower third. The slow contractions of the smooth muscle in this area allow food to pass into the stomach without the force generated by the skeletal muscle. The outer fibrous layer is called the adventitia, because it lacks an epithelial layer.

The esophagus is located just in front of the vertebral column and behind the trachea. It passes through the lower neck and thorax before penetrating the diaphragm and joining the stomach.

Each end of the esophagus is closed by a sphincter muscle when the tube is at rest and collapsed. The upper sphincter is the superior esophageal sphincter. Closing of this sphincter is caused not by active muscular contraction but rather by the passive elastic tension in the wall of the esophagus when the esophageal muscles are relaxed. The lower esophageal sphincter is a band of smooth muscle that includes the last 4 cm of the esophagus just before it connects to the stomach. The lower sphincter relaxes only long enough to allow food and liquids to pass into the stomach. The rest of the time, it is in a contracted configuration to prevent food and hydrochloric acid from being forced back into the esophagus when pressure increases in the abdomen. Such pressure usually increases when the abdominal muscles contract during the breathing cycle, during the late stages of pregnancy, and during the normal stomach contractions during digestion. If the lower esophageal sphincter does not close, the hydrochloric acid in the stomach may be forced up into the lower esophagus. The resultant irritation of the lining of the esophagus is known as heartburn, called this because it is a painful sensation and appears to be located near the heart. Damage to the lining of the esophagus caused by that hydrochloric acid known as acid reflux, and abbreviated "GERD", that causes the normal cells that line the esophagus, those cells being called the squamous cells, to turn into a type of cell not usually found in humans, called specialized columnar cells. That conversion of cells in the esophagus by the acid reflux, is known as Barrett's Esophagus. Symptoms of such a condition may include waking during the night because of a heartburn pain, vomiting, blood in the vomit or stool, and in difficulty with swallowing.

The diagnosis of such a condition involves the use of an endoscope inserted down the esophagus to as to evaluate the lining thereof, and to permit a biopsy to be taken of the tissue therein. This treatment is called an endoscopy, wherein the doctor thus guides the thin endoscopic tube through the mouth and into the esophagus. The scope may contain instruments that permit the doctor to see the lining of the esophagus and to remove a small sample of tissue from the esophagus lining. That tissue sample, called a biopsy, would be examined to see whether the normal squamous cells have been replaced with the columnar cells.

Cells in the lining of the esophagus, after having turned into columnar cells, will not revert back to normal squamous cells. There is, unfortunately, no cure presently for Barrett's Esophagus. Present treatment of this disease is effected to attempt to prevent further damage by stopping any additional acid reflux from the stomach. Some types of medications may be helpful, such as H2 receptor antagonists and proton pump inhibitors, which reduce the amount of acid produced by the stomach. There is a risk of developing cancer by about 5 to 10 percent of the people who have Barrett's Esophagus.

It is an object of the present invention to provide a treatment for patients who have Barrett's Esophagus disease.

It is a further object of the present invention to provide an arrangement to reverse abnormal columnar epithelial cells and secretory lining in the esophagus, to become the normal "whitish" squamous type of cell through precise modification of the lesion's vasculature.

It is yet a further object of the present invention to provide an optical radiation source which takes advantage of the optical differentiation of abnormal and normal tissue lining the esophagus to provide a treatment for that abnormal cellular condition.

BRIEF SUMMARY OF THE INVENTION

The present invention relates to several preferred embodiments for the treatment of Barrett's Esophagus, a first preferred embodiment including a light transmissiant apparatus which is arranged to extend through the patient's esophagus and direct selected pulses of optical radiation (i.e. light) through a wave guide and out a directable optical tip to be aimed onto selected portions of the patient's esophageal wall which wall portions include both particular cellular targets such as lesions and normal cells in the wall at the lower end of that esophagus.

Another preferred embodiment of that optical radiation delivery apparatus includes a wave guide arranged through an endoscope. The endoscope is guided down into the patient's esophagus. The wave guide has a laser source arranged at its proximalmost end, comprising a flashlamp housed adjacent a reflector. An optical filter and condensor lens directs the optical radiation through the wave guide arranged within the endoscope and then to the distal end of that wave guide which extends distally from the endoscope. The endoscope has viewing capabilities at its proximal end with an illuminator and an optical viewing lumen as well, to permit the attending physician to manipulate and directionally guide the distal end of the light guide optics. The distal end of the wave guide comprises the discharge means for the optical radiation passed therethrough. The distal end of the wave guide may be adapted to engage in direct physical contact with the spot or tissue to be treated, or may be held a spaced distance thereapart for directed treatment of light thereon.

The wave guide itself may be comprised of a liquid-containing lumen, which directs the optical radiation such as light, from its proximalmost end at the laser source to the distribution end at its distalmost portion.

Light-emitting diodes (LEDs) for light treatment of the patient comprises yet a further light-treatment embodiment of the optical radiation source of the present invention. In that embodiment, the light-emitting diodes would have power cables to a power source at the proximal end of the endoscope. Such a light apparatus included within that endoscope, which endoscope includes a visual optic guide, and an illumination lumen, provides light for the guiding physician to utilize the LEDs as light treatment apparatus.

An optical coupler may be arranged on the distal end of the endoscope as another embodiment. The optical coupler may have a prism thereon which includes a collimating optic on its side face. The prism and collimating optic are in communication with the optical fiber running down the endoscope. The optical coupler may have a key extending proximally therefrom, which key mates with a keyway arranged on the distal end of the endoscope. Rotation of the endoscope would thus affect rotation of the optical coupler for improved sensing and treatment of the epithelial cells on the lowermost portion of the esophagus.

The distal tip of the endoscope may in a further light-treatment embodiment include a LED light projection source arranged therewithin for distributing light through a grid and lens arrangement onto the treatment site.

If a laser is to be utilized within the present treatment arrangement, the wave or light guide is preferably made of a glass or a quartz core. Flexibility of the light guide is important. Such a light guide may have between 100 to 1,000 microns in diameter to permit such flexibility. A laser source should be specifically designed to treat vessels and be selectively absorbed by blood inside those vessels. Such a laser source may have wavelengths in the range of between 530 to 600 nm. Preferably a pulsed dye laser having a wavelength of 580 to 600 nm with a pulse duration of 0.35 to 100 ms. A further light source may be considered such as a filtered arc lamp or laser diodes or light emitting diodes. Dye lasers with a wavelength of 585 nm and a 0.5 ms pulse duration and a fluence range of 4 to 1000 J/cm$^2$ is preferred. Dosimetry is important in the treatment of cellular structure within the esophagus. Divergence of the delivered laser beam is minimized for an accurate fluence on the tissue being treated. To provide an accurate fluence delivery to the tissue being treated, a depth of field projection may be displayed onto the target site. The treatment fiber would extend out the distal tip of the endoscope and indicate an image size on the tissue site, indicating the appropriate distance from the treatment fiber to the target. This will ensure consistent spot size for optimizing the treatment of that target tissue.

A further preferred embodiment comprises the use of a contact tip on the distalmost end of the light guide, which tip may be longitudinally displacable. Precise dosimetry is thus guaranteed when the contact tip is in touching contact with the lesion on the esophagus wall.

Thus, what has been shown is an arrangement for the treatment of Barrett's Esophagus by vascular laser light absorption for selective photothermolysis, in which a light pulse is tailored to heat certain blood-containing targets which will have absorbed the energy and coagulated the target vessels killing the abnormal columnar epithelial cells lining the esophagus, a condition present in Barrett's Esophagus. Thus the adjacent normal tissue in the esophagus that contains no chromophores absorb the treatment optical radiation, is unharmed by that optical radiation therapy.

The invention thus comprises a method for the treatment of Barrett's Esophagus to reverse abnormal columnar epithelial cells and secretory lining in the esophagus of a patient having as a target, red secretory esophageal lining complications The steps include: connecting a wavelength specific optical radiation energy source to an elongated wave guide having a distal end, the wave guide arranged within a lumen of a steerable endoscope; guiding the endoscope into the esophagus of the patient; energyzing the optical energy source; manipulating the distal end of the light source onto a target on the endothelial complications inside of the esophagus for the selective thermolysis of the target in the esophagus; causing the red secretory esophogeal lining to revert to normal tissue, wherein the optical radiation has a fluence range of 4–1000 J/cm$^2$. The optical radiation energy source may comprise a pulse dye laser. The pulsed dye laser may have a wavelength range of about 580–600 nm. The optical radiation energy source may comprise light emitting diodes or a diode laser. The distal end of the optical radiation energy source may have an optical coupler thereon. The optical coupler may include a prism in light communication with the wave or light guide to direct a treatment light to the target site. The method may include: moving the distal end of the optical radiation energy source towards and/or away from the red secretory target lining of the esophagus to focus the light thereon, touching the red secretory lining of the esophagus by the light source to insure proper light contact dosimetry thereof. The light treatment energy may have an energy density of about 4–1000 J/cm$^2$.

The invention may also include a method for the treatment of Barrett's Esophagus to reverse abnormal columnar epithelial cells and secretory lining in the esophagus of a patient having a target of those abnormal cells comprising a red secretory esophageal lining complications. The method may comprise: connecting a wavelength specific optical radiation energy source to an elongated wave guide having a distal end, the wave guide arranged within a lumen of a steerable endoscope; guiding the endoscope into the esophagus of the patient; energyzing the optical energy source to generate a beam of light energy; manipulating the distal end of the light source onto the red secretory lining target comprising the endothelial complications inside of the esophagus for the selective thermolysis of the red secretory lining in the esophagus; causing the red secretory esophogeal to revert to a normal non-secretory "whitish" tissue by maintenance of the energyzing of the optical energy source, wherein the optical radiation has a fluence range of 4–1000 J/cm$^2$ and is inversely proportional to its spot size. The spot size of said beam of light energy has a range of between 0.4 mm. to 10 mm. in diameter.

The optical radiation energy source may comprise a pulse dye laser. The pulse dye laser may have a wavelength of about 580–600 nm. The optical radiation energy source may comprise light emitting diodes or a diode laser. The distal end of the optical radiation energy source may have an optical coupler thereon.

BRIEF DESCRIPTION OF THE DRAWINGS

The objects and advantages of the present invention will become more apparent when viewed in conjunction with the following drawings in which.

DESCRIPTION OF THE PREFERRED EMBODIMENTS

Figure 1:
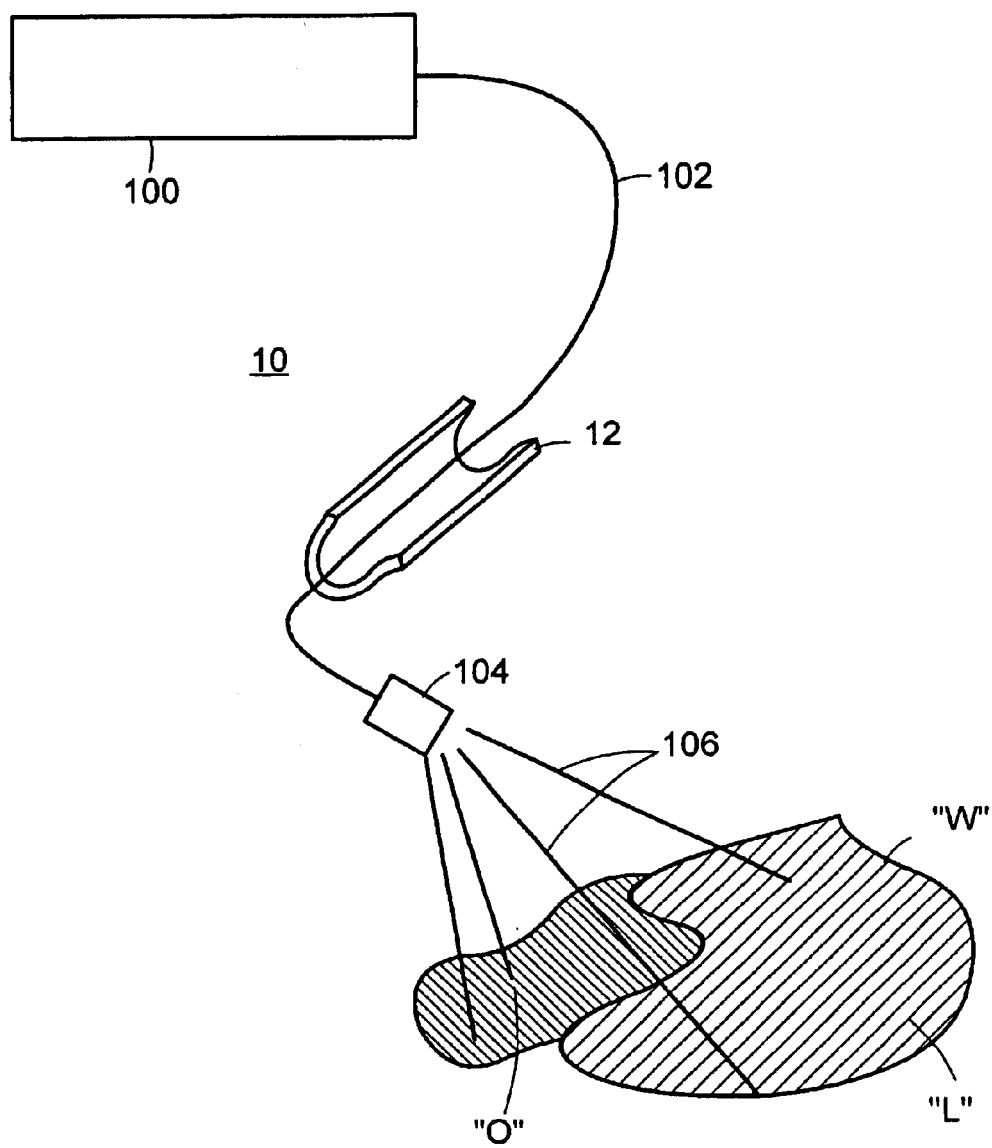
FIG. 1 is a diagrammatical representation of the light treatment by the present invention applied to both a lesion and unaffected tissue.

Referring now to the drawings in detail, and particularly to FIG. 1, there is shown a generic preferred embodiment the present invention which comprises an optical radiation (i.e. light) delivery apparatus 10 for the treatment of Barrett's Esophagus, wherein a light transmissiant apparatus 100 which is arranged to extend through the patient's esophagus 12 and direct selected pulses of optical radiation 106 (i.e. light) through a wave guide 102 and out a directable optical tip 104 to be aimed onto selected portions of the patient's esophageal wall "W" which wall portions include both particular (treatable) cellular targets "L" such as lesions as well as normal cells "O" (oblivious to the treatment optical radiation 104) in the wall "W" at the lower end of that esophagus 12. Since the unaffected (disease free, normal) tissue also receives treatment light 106, it is of minor consequence because that tissue "O" contains an insignificant quantity of chromophores, and is thus unaffected by such treatment light 106.

Figure 2:
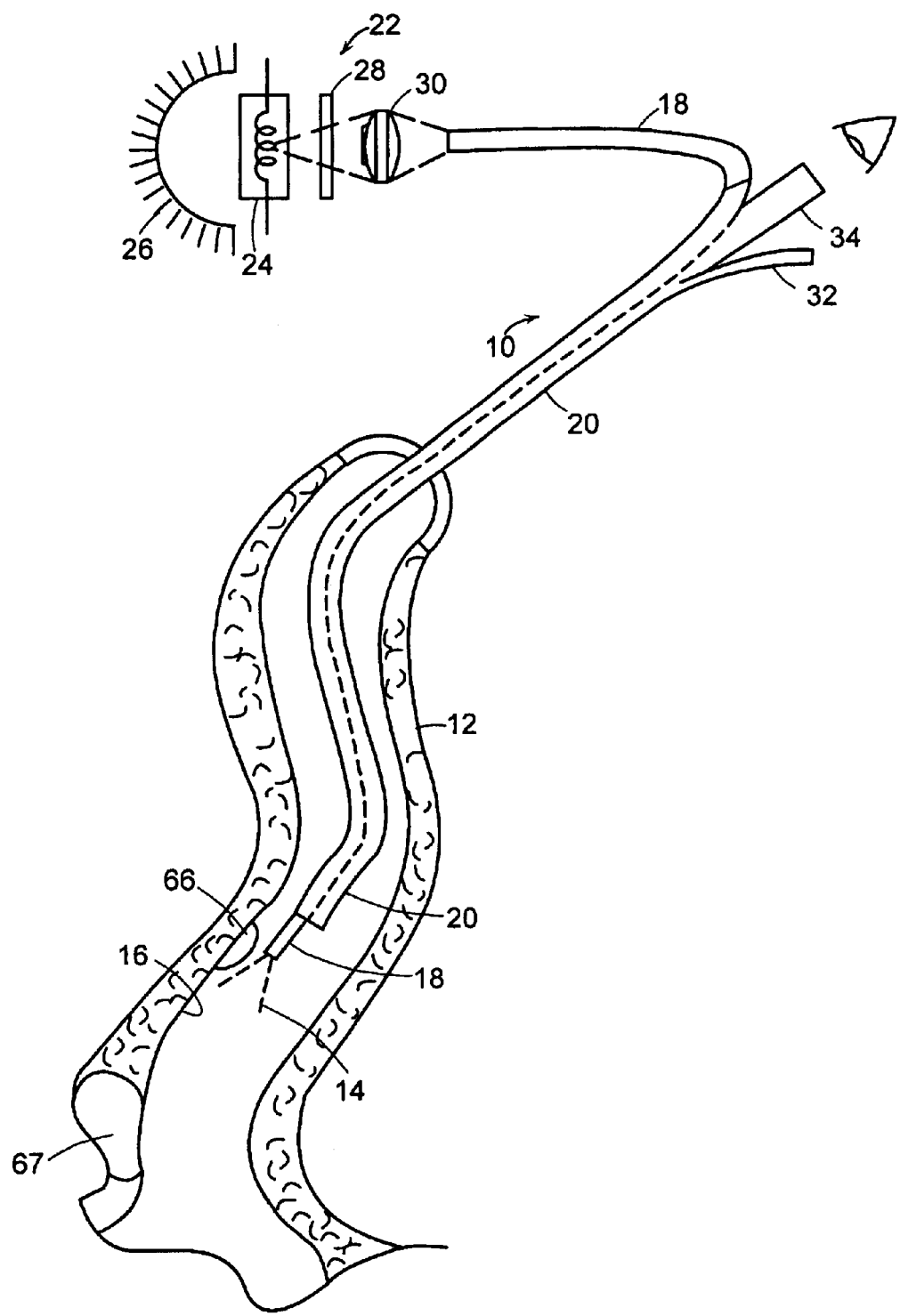
FIG. 2 is a schematic representation of a flashlamp for treatment with a light source utilized with a light guide and endoscope threaded through an esophagus for treatment thereof.
Figure 4:
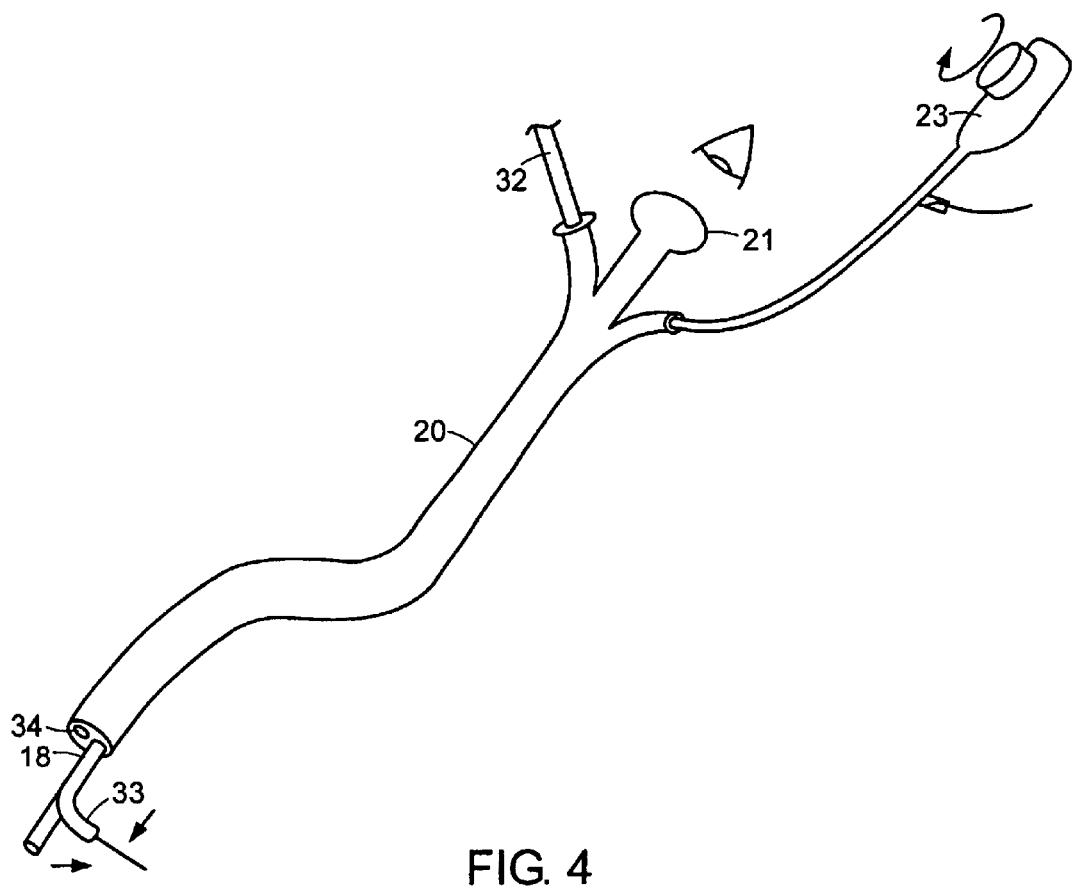
FIG. 4 is a representation of an endoscope and an energy dispensing manipulable tip therewith.
Figure 5:
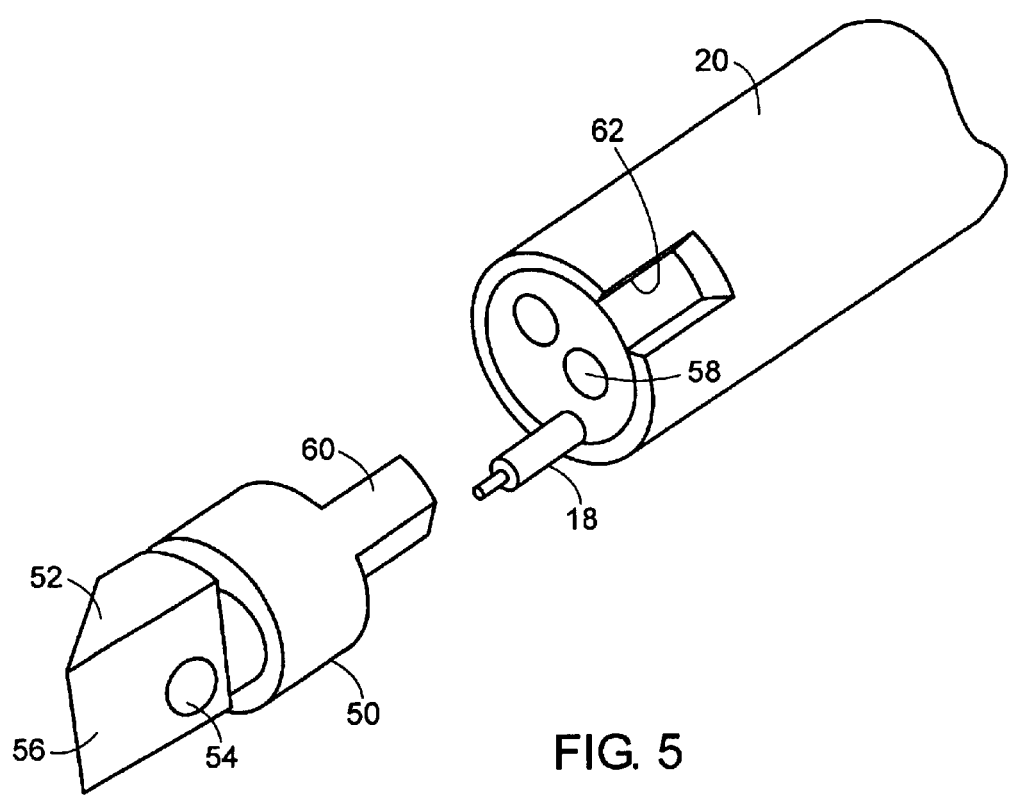
FIG. 5 is an exploded perspective representation of an energy directing tip that is adaptable to the distal end of a fiber extending from an endoscope.
Figure 6:
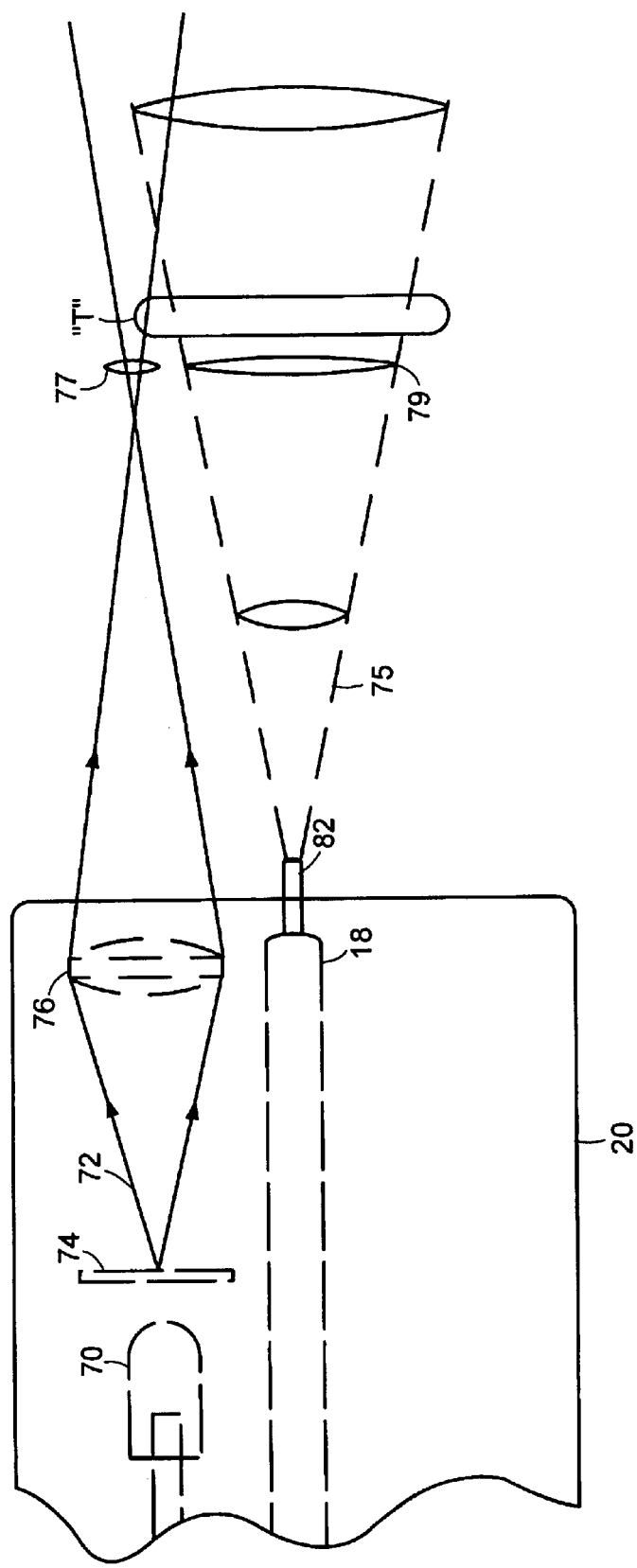
FIG. 6 is a plan view of the distal tip of a scope and image plane representation therewith as a spot size control arrangement.
Figure 7:
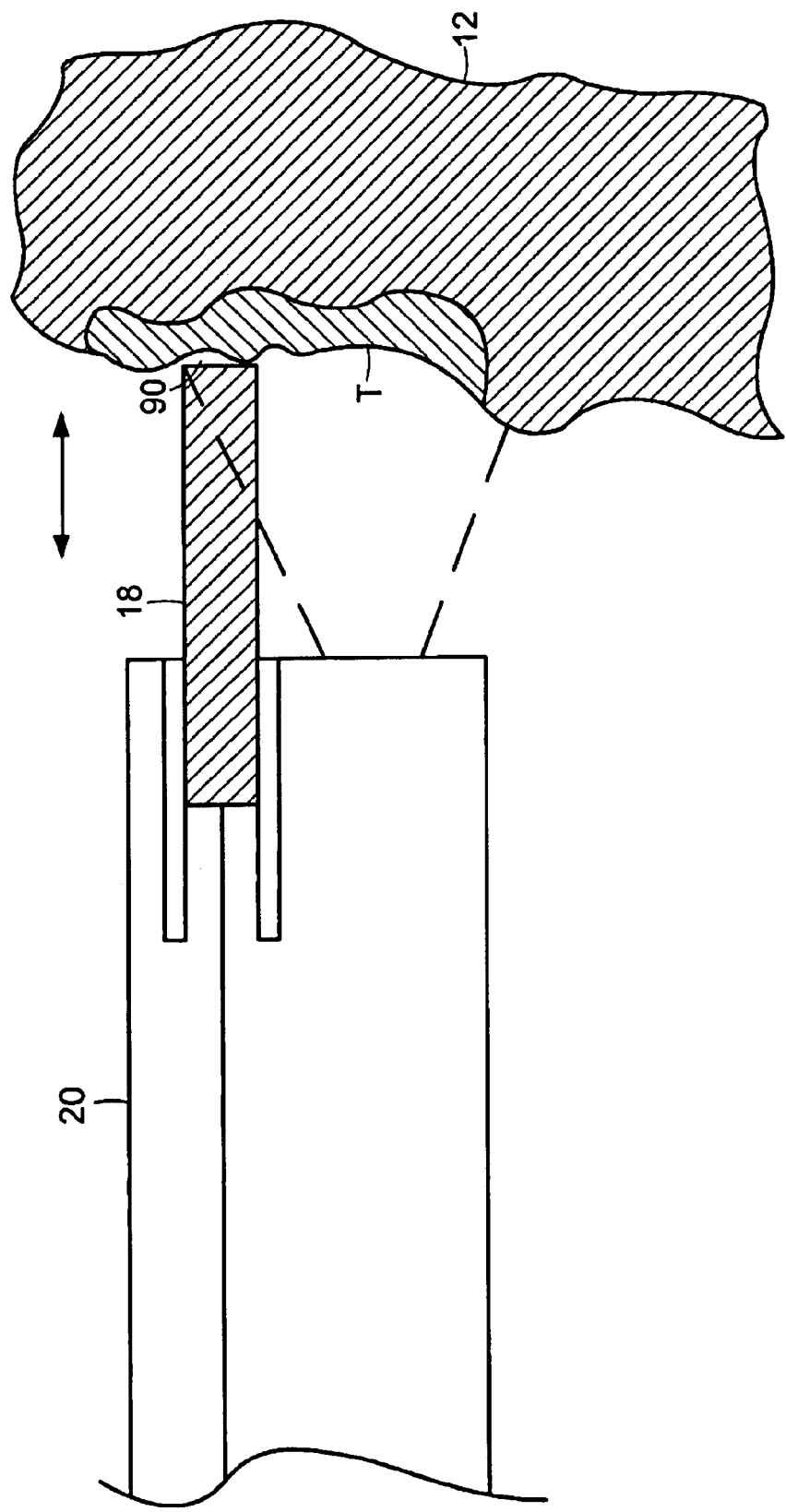
FIG. 7 is a side view of an endoscope with a contact tip for contactable treatment of a lesion within an esophagus.

A more specific preferred embodiment of that optical radiation delivery apparatus 10 includes a wave or light guide 18 arranged through an endoscope 20. The endoscope 20 is guided down into the patient's esophagus 12, as is represented in FIG. 2. The light guide 18 has an optical radiation source 22 arranged at its proximalmost end, in this embodiment, comprising a flashlamp 24 housed adjacent a reflector 26. An optical filter 28 and condenser lens 30 directs the optical radiation through the wave guide 18 arranged within the endoscope 20 and then to the distal end of that wave guide 18 which extends distally from the endoscope 20, as depicted in FIGS. 2, 4 and 5. The endoscope 20 has a viewing port 21 and a steering mechanism 23 at its proximal end with a target site illuminator 32 and an optical viewing lumen 34 as well, to permit the attending physician to manipulate and directionally guide the distal end of the light guide optics 33, as represented in FIG. 4. The distal end of the light guide 18 comprises the discharge means for the light passed therethrough. The distalmost end 90 of the wave guide 18 may be adapted to engage in direct physical contact with the spot or tissue to be treated, as represented in FIG. 7, or may be held a spaced distance thereapart for directed treatment of light thereon, as represented in FIG. 6 to permit the optical radiation treatment beam 75 to be adjustably "sized" to a proper diameter corresponding to the focused grid or image 77 from a light projection source 70.

In one embodiment of the wave guide 18, it may be comprised of a liquid-containing lumen, which lumen utilizes a liquid therein to direct the light from its proximalmost end at the laser source to the light treatment distribution end at its distalmost portion.

Figure 3:
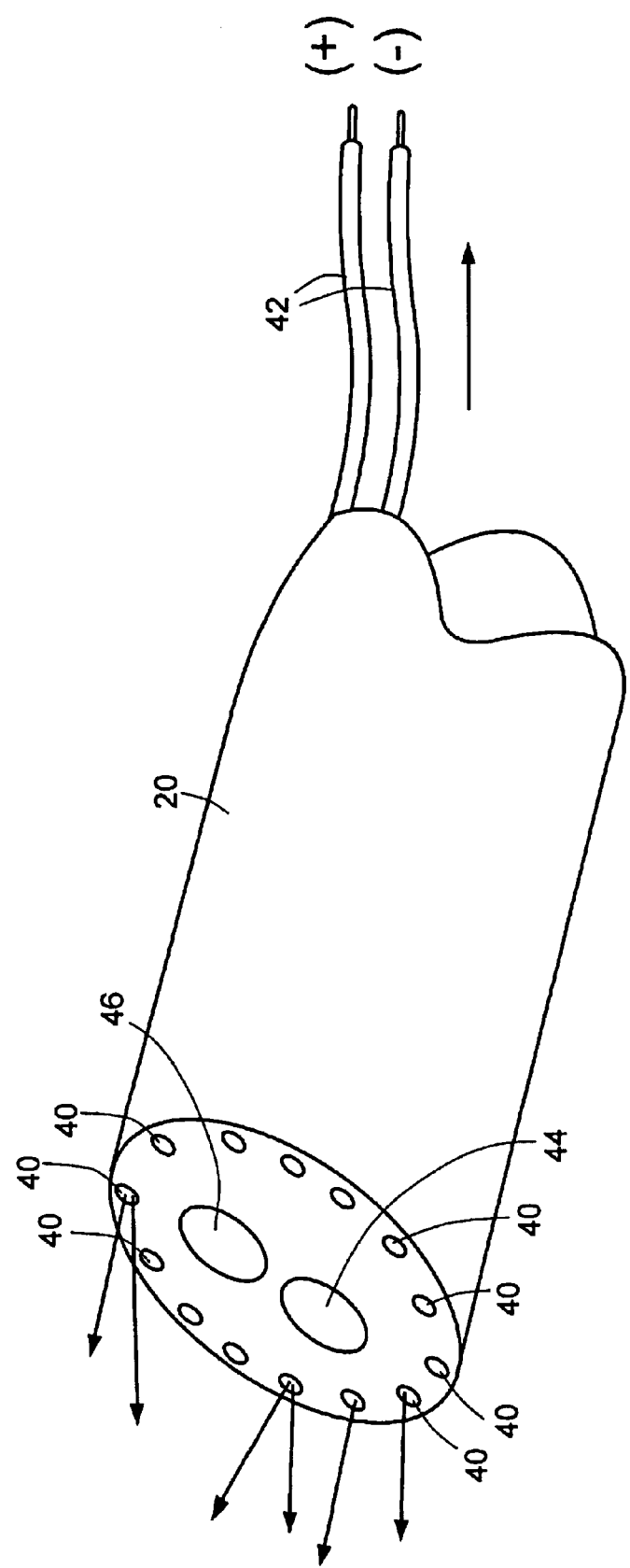
FIG. 3 is a perspective representation of the distal tip of the endoscope carrying an array of LEDs for the light treatment.

A further preferred embodiment is shown in FIG. 3, wherein an array of light-emitting diodes (LEDs) 40 comprise the treatment optical radiation source of the present invention. In that embodiment, the light-emitting diodes 40 would have power cables 42 to a power source at the proximal end of the endoscope 20. Such an LED optical radiation generation apparatus included within that endoscope 20 would also include a visual optic guide 44, and an illumination lumen 46 to provide light for the guiding physician to utilize and thereby guide the LEDs as a light treatment apparatus.

Shown in FIG. 5 is a removably adjustable optical coupler 50 that is arranged on the distal end of the endoscope 20. The optical coupler 50 may have a directional prism 52 thereon which includes a collimating optic 54 on its side face 56. The prism 52 and collimating optic 54 are in optical communication with the wave guide 18 and the optical fiber 58 running down the inside of the endoscope 20. The optical coupler 50 may have a key 60 extending proximally therefrom, which key 60 mates with a keyway 62 arranged on the distal end of the endoscope 20. Rotation of the endoscope 20 would thus effect rotation of the optical coupler 50 for improved sensing and treatment of the epithelial cells 66 on the lowermost portion of the esophagus 12, above the sphincter 67, as depicted in FIG. 1.

In FIG. 6, the distal tip of the endoscope 20 is shown including a LED light source 70 arranged therewithin, distributing light 72 through a grid 74 and a lens 76 arrangement as a grid pattern onto the treatment site lesion "T", for adjustable "sizing" comparison with a size and intensity adjustable treatment beam 75, as viewed and controlled by the attending physician through adjacent viewing optics, not shown for simplicity of the figure. The focused image 77 thus indicates the correct focal plane 79 in which the optical radiation (laser) may be fired with precise dosimetry.

If a laser is to be utilized within the present treatment arrangement, the light guide is preferably a glass or a quartz core. Flexibility of the light guide is important. Such a light guide may have between 100 to 1,000 microns in diameter to permit such flexibility. A laser source should be specifically designed to treat vessels and be selectively absorbed by blood inside those vessels. Such a laser source may have wavelengths in the range of between 530 to 600 nm. Preferably a pulsed dye laser having a wavelength of 580 to 600 nm with a pulse duration of 0.35 to 100 ms. A further light source may be considered such as a filtered arc lamp or laser diodes or light emitting diodes. Dye lasers with a wavelength of 585 nm and a 0.5 ms pulse duration and an fluence of 4 to 1000 J/cm$^2$ is preferred. Dosimetry is important in the treatment of cellular structure within the esophagus. Divergence of the delivered laser beam 75 is minimized for an accurate fluence on the target tissue. To provide an accurate fluence delivery to the tissue being treated, a grid or depth of field projection 79 may be displayed onto the target site "T" by a treatment fiber 82, as shown in FIG. 6. The treatment fiber 82 would extend out the distal tip of the endoscope 20 and indicate an image size on the tissue site, indicating the appropriate distance from the light source to the target "T" as aforementioned. This will ensure consistent spot size for optimizing the treatment of that target tissue. Such treatment is possible because there is a distinct optical differentiation of abnormal and normal tissue. The redness of the target lesion defines the use of a light source which targets red-hemoglobin.

FIG. 7 shows a further embodiment using a longitudinally displaceable contact tip 90 on the distalmost end of the light or wave guide 18. Precise dosimetry is guaranteed when the contact tip 90 is in touching contact with the lesion "T" on the wall of the esophagus 12.

Figure 8:
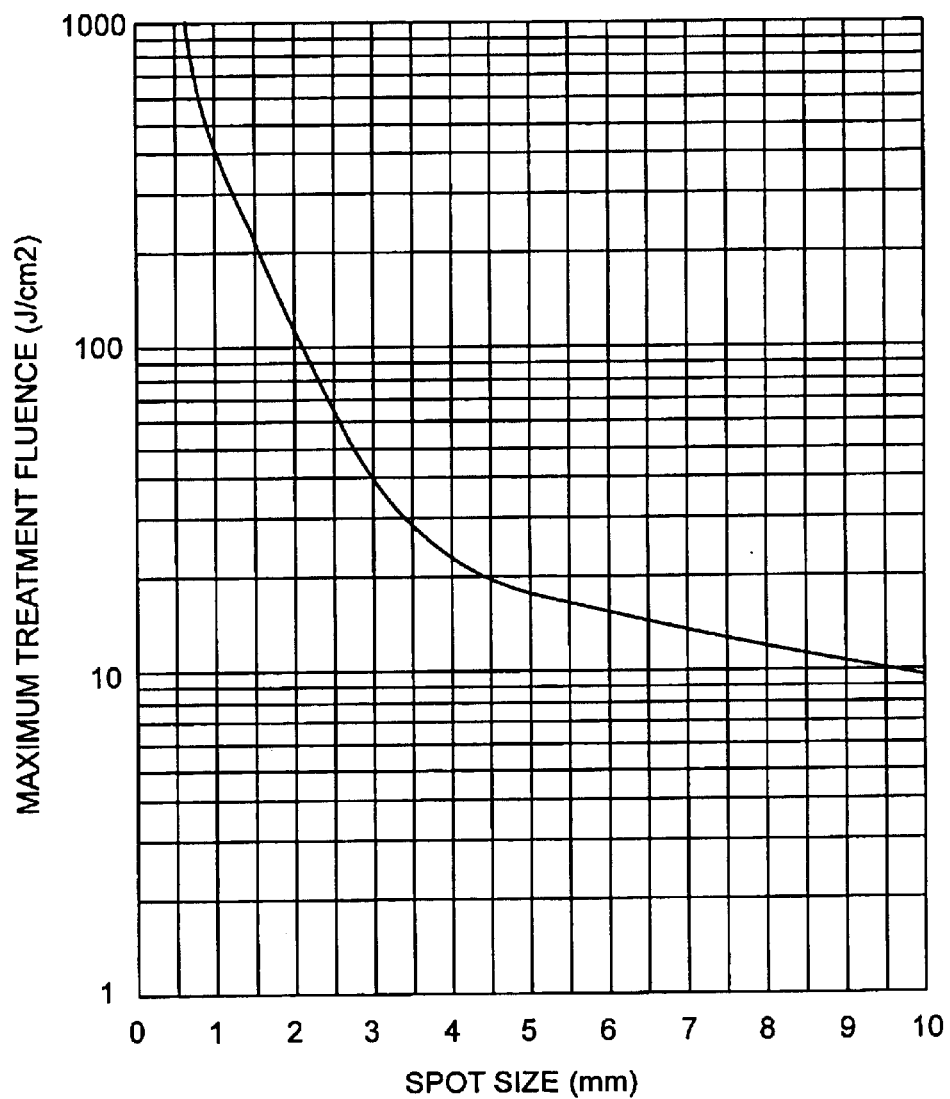
FIG. 8 is a chart showing the relationship between maximum treatment fluence and spot size.

A graph showing the relationship of maximum treatment fluence to spot size of the treatment radiation is shown in FIG. 8. The fluence may be as high as 1000 J/cm$^2$, depending on the size in mm. of the optical radiation. Because of the wavelength and pulse duration and the target chromophores, the relatively high fluences are tolerated by adjacent, struck, non-target tissues.

Thus, what has been shown is an arrangement for the treatment of Barrett's Esophagus by vascular laser light absorption for selective photo thermolysis. A pulse of optical radiation (i.e. light) is thus tailored to heat certain blood-containing targets which will have absorbed the light energy and coagulate the target's blood vessels. The killing of the abnormal columnar epithelial cells lining the esophagus is thus accomplished by the treatment for Barrett's Esophagus as proposed by the present invention, without harming adjacent non-diseased tissue.

We claim:

1. A method for the treatment of Barrett's Esophagus to reverse esophageal lining disease comprising at least one of abnormal epithelial cells and secretory lining in the esophagus of a patient having red secretory esophageal lining disease, the method comprising:

connecting a wavelength specific optical radiation energy source to an elongated wave guide having a distal end with an optical coupler thereon, said wave guide arranged within a lumen of a steerable endoscope, said optical coupler arranged with said wave guide to direct a treatment radiation to a target site;

guiding said endoscope into the esophagus of the patient;

energizing said optical energy source consisting of a pulsed dye laser to generate an optical radiation treatment beam;

manipulating said distal end of said wave guide onto a target on said disease inside of said esophagus for the selective thermolysis of said target in said esophagus by said optical radiation treatment beam; causing said red secretory esophogeal lining to revert to normal tissue, wherein said optical radiation treatment beam has a fluence range of 4–1000 J/cm$^2$;

moving said distal end of said wave guide towards and away from said red secretory lining of the esophagus to focus said optical radiation thereon; and arranging a grid pattern on said red secretory lining of the esophagus by a separate light source to permit a focused image for comparison with said treatment beam.

2. The method as recited in claim 1, wherein said pulse dye laser has a wavelength range of about 580–600 nm.

3. The method as recited in claim 1, wherein said optical coupler includes a prism in communication with said light guide to direct a treatment radiation to a target site.

4. The method as recited in claim 1, including: touching said red secretory lining of the esophagus by said wave guide to insure proper treatment beam contact dosimetry thereof.

5. A method for the treatment of Barrett's Esophagus to reverse esophageal lining disease comprising at least one of abnormal columnar epithelial cells and secretory lining in the esophagus of a patient having red secretory esophageal lining disease, the method comprising:

connecting a wavelength specific optical radiation energy source consisting of a pulsed dye laser to an elongated wave guide having a distal end with an optical coupler thereon, said coupler arranged in communication with said wave guide arranged within a lumen of a steerable endoscope;

guiding said endoscope into the esophagus of the patient;

energizing said optical energy source to generate a beam of light energy;

manipulating said distal end of said wave guide onto said red secretory lining comprising said disease inside of said esophagus for the selective thermolysis of said red secretory lining in said esophagus; causing said red secretory esophageal lining to revert to a normal non-secretory "whitish" tissue by maintenance of said energizing of said optical energy source, wherein said optical radiation has a fluence range of 4–1000 J/cm$^2$ and is inversely proportional to its spot size; moving said distal end of said wave guide towards and away from said red secretory lining of the esophagus to focus said optical radiation thereon; and arranging a grid pattern on said red secretory lining of the esophagus by a separate light source to permit a focused image for comparison with said treatment beam.

6. The method of claim 5, wherein said spot size of said beam of light energy has a range of between 1 mm. to 10 mm. in diameter.

7. The method as recited in claim 5, wherein said pulsed dye laser has a wavelength of about 580–600 nm.

8. A method for the treatment of Barrett's Esophagus to reverse esophageal lining disease comprising at least one abnormal columnar epithelial cells and secretory lining in the esophagus of a patient having red secretory esophageal lining disease, the method comprising:

connecting a wavelength specific optical radiation energy source to an elongated wave guide having a distal end, said wave guid within a lumen of a steerable endoscope;

guiding said endoscope into the esophagus of the patient;

energizing said optical energy source to generate an optical radiation treatment beam; and directing said distal end of said wave guide onto a target on said disease inside of said esophagus for the selective thermolysis of target in said esophagus by said optical radiation treatment beam; the wavelength and fluence of the optical radiation treatment beam selected to heat blod vessels and destroy abnormal cells of the red secretory esophogeal lining without significantly harming normal tissue in the target area, said optical radiation treatment beam having a fluence range of 4–1000 J/cm$^2$.

9. The method as recited in claim 8, wherein said optical radiation energy source comprises a plused dye laser.

10. The method as recited in claim 9, wherein said plused dye laser has a wavelength range of about 580–600 nm.

11. The method as recited in claim 8, wherein said optical radiation energy source comprises at least one light emitting diode.

12. The method as recited in claim 8, wherein said distal end of said wave guide comprises an optical coupler.

13. The method as recited in claim 12, wherein said optical coupler includes a prism in communication with said wave guide to direct a treatment radiation to a target size.

14. The method as recited in claim 8, further comprising:
moving said distal end of said wave guide towards and away from said red secretory lining of the esophagus to focus said optical radiation thereon;
arranging a grid pattern on said red secretory lining of the esophagus by a separate light souce to permit a focused image for comparison with said treatment beam.

15. The method as recited in claim 8, further comprising touching said red secretory lining of the esophagus by said wave guide to insure proper treatment beam contact dosimetry thereof.

16. The method as recited in claim 15 wherein said wave guide is between 100 and 1,000 microns in diameter.

17. A method for the treatment of Barrett's Esophagus to reverse esophageal lining disease comprising at least one of abnormal columnar epithelial cells and secretory lining in the esophagus of a patient having red secretory esophageal lining disease, the method comprising:
connecting a wavelength-specific optical radiation energy source to an elongated wave guide having a distal end, said wave guide arraged within a lumen of a steerable endoscope;
guiding said endoscope into the esophagus of the patient;
energizing said optical energy source to generate a beam of light energy;
directing said distal end of said wave guide said red secretory lining comprising said disease inside of said esophagus for the selective thermolyisis of said red secretory lining in said esophagus; and causing the red secretory esophageal lining to revert to a normal non-secretory "whitish" tissue by maintenance of said energizing of said opitcal energy source, the wavelength and fluence of the optical radiation treatment beam selected to heat blood vessels and destory abnormal cells of the red secretory esophageal lining without significantly harming mornal tissue in the target area; wherein said optical radiation has a fluence range of 4–1000 J/cm$^2$ and is inversely proportional to its spot size.

18. The method of claim 17, wherein said spot size of said beam of light energy has a range of between 1 mm to 10 mm. in diameter.

19. The method as recited in claim 17, wherein said optical radiation energy source comprises a pulsed dye laser.

20. The method as recited in claim 19, wherein said plused dye laser has a wavelength of about 580–600 nm.

21. The method as recited in claim 17, wherein said optical radiation energy source comprises light emitting diodes.

22. The method as recited in claim 17, wherein said distal end of said wave guide is an optical coupler.

23. The method as recited in claim 22, wherein said optical coupler includes a prism in light communication with said wave guide to direct a treatment light to a target site.

24. The method as recited in claim 17, further comprising moving said distal end of said wave guide towards and away from said red secretory lining of the esophagus to focus said optical energy radiation thereon.

25. A method for the treatment of Barrett's Esophagus to reverse esophageal lining disease comprising at least one of abnormal columnar epithelial cells and secretory lining in the esophagus of a patient having red secretory esophageal lining disease, the method comprising:
connecting a wavelength specific optical radiation energy source to an elongated wave guide having a distal end with an optical coupler thereon, said optical coupler comprising a prism in communication with said wave guide arranged within a lumen of a steerable endoscope;
guiding said endoscope into the esophagus of the patient;
energizing said optical energy source to generate a beam of light energy;
manipulating said distal end of said wave guide onto said red secretory lining comprising said disease inside esophagus for the selective thermolysis of said red secretory lining in said esophagus; causing said red secretory esophageal to revert to a normal "whitish" tissue by maintenance of said energizing of said optical energy source, wherein said optical radiation has a fluence range of 4–1000 J/cm$^2$ and is inversely proportional to its spot size; wherein said spot size of said beam of light energy has a range of between 1 mm to 10 mm in diameter, and said optical radiation energy source comprises a pulsed dye laser having a wavelength of about 580–600 nm;
moving said distal end of said wave guide towards and away from said red secretory lining of the esophagus to focus said optical radiation thereon; and
arraging a grid pattern on said red secretory lining of the esohpagus by a separate light source to permit a focused image for comparison with said treatment beam.

26. A method for the treatment of Barrett' Esophagus to reverse esophageal lining disease comprising at least one of abnormal columnar epithelial cells and secretory lining in the esophagus of a patient having red secretory esophageal lining disease, the method comprising:
connecting a wavelength specific optical radiation energy source to an elongated wave guide having a distal end, said wave guide arranged within a lumen of a steerable endoscope;
guiding said endoscope into the esophagus of the patient;
energizing said optical energy source to generate a beam of light energy;
manipulating said distal end of said wave guide to direct the beam of light energy onto said red secretory lining comprising said disease inside of said esophagus for the selective thermolysis of said red secretory lining in said esophagus;
causing said red secretory esophageal lining to revert to a normal "whitish" tissue by maintenance of said energizing of said optical energy source, wherein said optical radiation has a fluence rang of 4–1000 J/cm$^2$ and is inversely proportional to its spot size; mm. in diameter, and said optical radiation energy source comprises a pulsed dye laser having a wavelength of about 500–600 nm.
causing said red secretory esophageal ining to revert to a normal "whitish" tissue by maintenance of said energizing of said optical energy source, wherein said optical radiation has a fluence range of 4–1000 J/cm$^2$ and is inversely proportional to its spot size; wherein said spot size of said beam of light energy has a range of between 1 mm to 10 mm in diameter, and said optical radiation energy source comprises a pulsed dyer laser having a wavelength of about 580–600 nm.

* * * * *

UNITED STATES PATENT AND TRADEMARK OFFICE
CERTIFICATE OF CORRECTION

PATENT NO. : 7,066,930 B2
APPLICATION NO. : 10/118283
DATED : June 27, 2006
INVENTOR(S) : James H. Boll and George E. S. Cho It is certified that error appears in the above-identified patent and that said Letters Patent is hereby corrected as shown below:

Column 7
In Claim 2, line 63, delete "pulse" and insert -- pulsed --.

Column 8
In Claim 8, lines 40 through 41, delete "one abnormal" and insert -- one of abnormal --.

Column 8
In Claim 8, line 46, delete "guid" and insert -- guide --.

Column 9
In Claim 13, line 5, delete "size" and insert -- site --.

Column 9
In Claim 17, line 34, delete "the" and insert -- said --.

Column 9
In Claim 17, line 41, delete "mornal" and insert -- normal --.

Column 10
In Claim 25, lines 11 through 12, delete "inside esophagus" and insert -- inside of said esophagus --.

Column 10
In Claim 26, line 52, delete "rang" and insert -- range --.

Column 10
In Claim 26, lines 53 through 56, delete "mm. in diameter, and said optical radiation energy source comprises a pulsed dye laser having a wavelength of about 500-600 nm." and insert -- wherein said spot size of said beam of light energy has a range of between 1 mm. To 10 mm. In diameter, and said optical radiation energy source comprises a pulsed dye laser having a wavelength of about 580-600 nm. --.

UNITED STATES PATENT AND TRADEMARK OFFICE
CERTIFICATE OF CORRECTION

PATENT NO. : 7,066,930 B2
APPLICATION NO. : 10/118283
DATED : June 27, 2006
INVENTOR(S) : James H. Boll and George E. S. Cho It is certified that error appears in the above-identified patent and that said Letters Patent is hereby corrected as shown below:

Column 10
In Claim 26, lines 57 through 65, delete "causing said red secretory esophageal ining to revert to a normal "whitish" tissue by maintenance of said energizing of said optical energy source, wherein said optical radiation has a fluence range of 4-1000 $J/cm^2$ and is inversely proportional to its spot size; wherein said spot size of said beam of light energy has a range of between 1 mm to 10 mm in diameter, and said optical radiation energy source comprises a pulsed dyer laser having a wavelength of about 580-600 nm."

Signed and Sealed this

Fifteenth Day of May, 2007

JON W. DUDAS
*Director of the United States Patent and Trademark Office*